United States Patent [19]

Zahn et al.

[11] Patent Number: 5,162,190

[45] Date of Patent: Nov. 10, 1992

[54] 1,2-NAPHTHOQUINONE-2-DIAZIDE-SULFONIC ACID AMIDES AND PHOTOSENSITIVE COMPOSITIONS CONTAINING THESE COMPOUNDS

[75] Inventors: Wolfgang Zahn, Eltville; Gerhard Buhr, Koenigstein; Hartmut Steppan, Wiesbaden, all of Fed. Rep. of Germany

[73] Assignee: Hoechst Aktiengesellschaft, Frankfurt am Main, Fed. Rep. of Germany

[21] Appl. No.: 373,036

[22] Filed: Jun. 29, 1989

[30] Foreign Application Priority Data

Jul. 4, 1988 [DE] Fed. Rep. of Germany ....... 3822522

[51] Int. Cl.$^5$ .................. G03F 7/022; G03F 7/023
[52] U.S. Cl. .................. 430/190; 430/165; 430/192; 430/193; 430/326; 534/556; 534/554
[58] Field of Search .............. 430/193, 192, 191, 189, 430/190; 534/556, 559

[56] References Cited

U.S. PATENT DOCUMENTS

| | | | |
|---|---|---|---|
| 3,046,110 | 7/1962 | Schmidt | 96/33 |
| 3,130,049 | 4/1964 | Neugebauer et al. | 430/193 |
| 3,269,837 | 8/1966 | Sus | 430/193 |
| 3,687,663 | 8/1972 | Bloom | 96/33 |
| 3,890,152 | 6/1975 | Ruckert et al. | 96/75 |
| 4,196,003 | 4/1980 | Watanabe | 430/193 |
| 4,308,368 | 12/1981 | Kubo et al. | 525/504 |
| 4,424,270 | 1/1984 | Erdman et al. | 430/166 |
| 4,555,469 | 11/1985 | Erdman et al. | 430/168 |
| 4,576,901 | 3/1986 | Stahlhofen et al. | 430/325 |
| 4,738,915 | 4/1988 | Komino et al. | 430/193 |
| 4,774,171 | 9/1988 | Zahn et al. | 430/192 |
| 4,816,380 | 3/1989 | Covington et al. | 430/193 |
| 4,871,645 | 10/1989 | Uenishi et al. | 430/192 |
| 4,975,351 | 12/1990 | Akaki et al. | 430/192 |

OTHER PUBLICATIONS

Fujy, G06, 87—338782/48, J6 2244—039—A, Fuji Yakuhin Kogyo Apr. 17, 1988, JP 088659, A89 E24 P83 P84 Oct. 24, 1987 G03c01/72 G03f—07/08.
Kons, G06, 87—009991/02, J6 1266—423—A, Konishiroku Photo KK, May 20, 1985 JP—109960 A21 E14 P83 P84 (A89) Nov. 26, 1986 C08g—08/32 G03c—01/72.
Fujf, G06, 85—214542/35, J6 0138—544—A, Fuji Photo Film KK Dec. 26, 1983 JP 252—064 A89 P83 P84 Jul. 23, 1985 G03c—01/72G03f—07/08.
Kons, G06, 87—010233/02, J6 1267—043—A, Konishiroku Photo KK May 21, 1985 JP 109689, A89 P83 P84 (A21) Nov. 26, 1986 G03c—01/72 G03f—07/02.
Dnin, G06, 86—328882/50, J6 1245—154—A, Dainippon Ink Chem KK Apr. 23, 1985 JP 086874, A89 U11 P83 P84, Oct. 31, 1986 G03c 01/72, G03f—07/08.
Kosar, J. "Light—Sensitive Systems", John Wiley and Sons, New York, 1965, pp. 343—351.

*Primary Examiner*—Charles L. Bowers, Jr.
*Assistant Examiner*—John S. Y. Chu
*Attorney, Agent, or Firm*—Foley & Lardner

[57] ABSTRACT

A compound of the general formula I

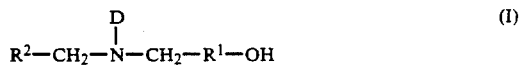

in which
D denotes a 1,2-naphthoquinone-2-diazide-4-sulfonyl or -5-sulfonyl radical,
$R^1$ denotes an alkylene group and
$R^2$ denotes a hydrogen atom, an alkyl group or a group $R^1$—OH, or of the general formula II

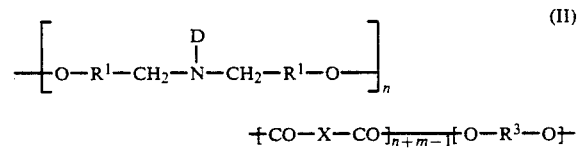

in which
X denotes an alkylene group, an arylene group or a group of the formula

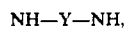

NH—Y—NH, wherein Y is an alkylene group or an arylene group,
$R^3$ denotes an alkylene group, which may be interrupted by ether oxygen atoms,
n is a number from 1 to 40 and
m is a number from 0 to 50,
the ratio m:(m+n) being from 0:100 to 95:100 and $R^1$ and D having the above-indicated meaning, are disclosed. The compounds may be used in positive-working photosenitive materials for the production of printing plates and photoresists. Compounds according to formula II do not require an addition of polymeric binders.

21 Claims, No Drawings

1,2-NAPHTHOQUINONE-2-DIAZIDE-SULFONIC ACID AMIDES AND PHOTOSENSITIVE COMPOSITIONS CONTAINING THESE COMPOUNDS

BACKGROUND OF THE INVENTION

The present invention relates to novel 1,2-naphthoquinone-2-diazide-sulfonic acid amides and photosensitive compositions and recording materials containing these compounds.

Many derivatives, in particular aromatic esters, of 1,2-naphthoquinone-2-diazide-sulfonic acids are known for use as photosensitive components in positive-working recording materials. In his book, *Light-Sensitive Systems*, published by John Wiley and Sons, New York, 1965, pages 343 to 351, Jaromir Kosar describes a number of photosensitive naphthoquinone diazides.

In the customary photosensitive compositions, the naphthoquinone diazides are combined with polymeric binders carrying phenolic hydroxyl groups. These binders are, in general, novolaks, which impart mechanical strength and resistance, but also a certain degree of brittleness, to the layers prepared from the photosensitive compositions.

In order to reduce this brittleness, it is necessary to use a smaller amount of novolaks in the photosensitive compositions or, if possible, to do entirely without novolaks as layer components. This has also the effect that problems which may occur in connection with the mixing or the solubility are obviated.

Monomeric naphthoquinone diazides alone do not form completely homogeneous layers and cannot be considered for use as coating materials. In order to be able to dispense with binders in these photosensitive compositions, polymeric naphthoquinone diazide derivatives must therefore be employed.

A number of polymeric naphthoquinone diazides have already been disclosed, in which the naphthoquinone diazide radical is linked by an ester group to the polymeric basic structure or to correspondingly functionalized side chains of the polymer. For example, DE-C-865 860 and EP-B-0 055 814 describe esters of naphthoquinone diazide sulfonic acids with phenolic resins. Similar compounds are disclosed in JP-A-86/267043, 86/266423, 85/138544 and 87/244039 and in U.S. Pat. No. 4,308,368. JP-A-86/245154 describes reaction products of naphthoquinone diazide sulfonyl chlorides with polyurethanes.

EP-A-0 231 855 describes bis-naphthoquinone diazide sulfonic acid amides of secondary diamines, which are, in particular, sensitive in the medium UV range.

In the above-indicated examples, as far as polymeric compounds are concerned, the naphthoquinone diazide radical is linked to a pre-prepared polymer structure in a polymer-analogous reaction and, in the process, attention must be paid to all known disadvantages of polymer-analogous reactions It is therefore more favorable to couple the incorporation of the naphthoquinone diazide group with the polymerization reaction, i.e., to use appropriate naphthoquinone diazide compounds as monomer units.

SUMMARY OF THE INVENTION

It is therefore an object of the present invention to provide novel monomeric and polymeric compounds having lateral naphthoquinone diazide radicals, that permit a more exact determination of the naphthoquinone diazide radicals contained in the polymer molecule and are suitable for the preparation of photosensitive compositions without the addition of binders.

These and other objects according to the invention are achieved by a compound of the general formula I

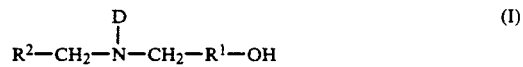

in which
- D denotes a 1,2-naphthoquinone-2-diazide-4-sulfonyl or -5-sulfonyl radical,
- $R^1$ denotes an alkylene group with 1 to 3 carbon atoms, and
- $R^2$ denotes a hydrogen atom, an alkyl group with 1 to 3 carbon atoms or a group $R^1$—OH, or of the general formula II

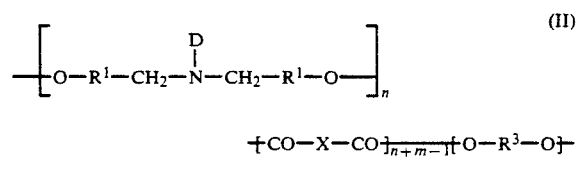

in which
- X denotes an alkylene group with 2 to 12 carbon atoms, an arylene group with 6 to 10 carbon atoms or a group of the formula

NH-Y-NH, wherein
- Y is an alkylene group with 2 to 12 carbon atoms or an arylene group with 6 to 14 carbon atoms,
- $R^3$ denotes an alkylene group with 2 to 12 carbon atoms, which may be interrupted by ether oxygen atoms,
- n is a number from 1 to 40, and
- m is a number from 0 to 50, the ratio m:(m+n) being from 0:100 to 95:100 and $R^1$ and D having the above-indicated meanings.

The invention also provides a photosensitive composition comprising a polymeric binder that is insoluble in water and soluble in organic solvents and in aqueous-alkaline solutions, and a 1,2-naphthoquinone-2-diazide-sulfonic acid amide. The composition according to the present invention comprises 5 to 100% by weight, based on its non-volatile components, of a compound as described above.

A photosensitive recording material is also provided according to the invention, comprising a support and a photosensitive layer comprising a compound as described above.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

In the recording material of the present invention the photosensitive layer contains a compound according to one of formulae I and II.

The monomeric compounds according to the invention corresponding to formula I can be used as such in photosensitive compositions, and it is then expedient to add an alkali-soluble polymeric binder to the composition, as is customarily done. These compounds are, in particular, also suitable for use as intermediate products for the preparation of the polymeric compounds of formula II. The properties of these polymers can be matched to the desired use by a deliberate, determined introduction of diol components HO—$R^3$—OH. Depending on the particular requirement it is also possible to do without an incorporation of neutral diol components, or the polymeric naphthoquinone diazides can be combined with non-photosensitive binders.

Of the compounds according to general formula I, those in which $R^2$ is hydroxyalkyl are preferred, if they are to be further processed into polymers. $R^1$ may be a straight-chain or branched radical and has advantageously 1 or 2 carbon atoms. The preferred alkyl groups $R^2$ comprise methyl groups.

In the general formula II, Y is preferably an alkylene group having from 4 to 10, in particular from 6 to 10, carbon atoms; the preferred arylene groups are mononuclear arylene groups. Suitable diisocyanates OCN-X-NCO comprise, for example, ethylene diisocyanate, butylene diisocyanate, hexamethylene diisocyanate, 2,2,4-trimethylhexamethylene diisocyanate, cyclohexylene diisocyanate, isophorone diisocyanate, tolylene diisocyanate, diphenylmethane diisocyanate and naphthalene diisocyanate.

If X is an alkylene group, the latter has advantageously 4 to 10 carbon atoms, the preferred arylene groups are phenyl groups. $R^3$ has preferably from 4 to 10, in particular from 4 to 8, carbon atoms. Examples of suitable diols HO—$R^3$—OH include ethylene glycol, propylene glycol, butanediol-1,4, hexamethylenediol, neopentyl glycol, 1,1,3-trimethyl-propanediol-1,3, diethylene glycol, triethylene glycol, pentaethylene glycol and tripropylene glycol. The ratio m:(m+n) is preferably in the range from 10:100 to 95:100, in particular from 25:100 to 90:100.

Compounds of the present invention corresponding to formula I may be prepared by reacting bis-hydroxyalkylamines with reactive naphthoquinone diazide sulfonic acid derivatives, such as the acid chloride, analogously to known processes.

Preferred processes which may be used are the reactions in inert solvents, such as ketones or chlorinated hydrocarbons, in the presence of inorganic or organic bases, such as sodium carbonate or tertiary amines, such as triethylamine. It is, however, also possible to prepare the naphthoquinone diazide sulfonic acid amides of the present invention under the conditions of phase-transfer catalysis, for example, in a mixture of methylene chloride with an aqueous solution of sodium carbonate or tetraalkylammoniumhydroxide using an appropriate catalyst, such as tetrabutylammonium bromide.

The following is a general instruction for the preparation of the monomeric naphthoquinone diazide sulfonic acid amides according to the present invention:

0.2 mol of dialkanolamine are added dropwise with stirring to 0.2 mol of 1,2-naphthoquinone-2-diazide sulfonic acid chloride and 0.22 mol of sodium carbonate or triethylamine in 400 ml of acetone, the temperature being kept below 25° C. by cooling. Upon completion of the dropwise addition, stirring is continued for 1 hour and a) if the naphthoquinone diazide sulfonic acid amide has already been deposited, the latter is filtered off by suction, washed with cold acetone and then with water and the filter residue is dried under reduced pressure or in a circulating air oven at a moderately elevated temperature, or b) if the naphthoquinone diazide sulfonic acid amide is completely soluble in the reaction mixture, the preparation is freed from inorganic constituents by suction filtration. The filtrate is stirred into ten times the quantity of a 4% strength aqueous hydrochloric acid, the precipitated sulfonic acid amide is filtered off, washed acid-free with water and dried as under a) above.

Reacting the monomeric naphthoquinone diazide sulfonic acid amides, which possess two hydroxyl groups, with bifunctional compounds, such as dicarboxylic acid dichlorides or diisocyanates, is carried out analogously to processes known in the art.

The reactions with dicarboxylic acid dichlorides are preferably run in inert solvents, such as ketones or chlorinated hydrocarbons, in the presence of inorganic or organic bases, such as potassium carbonate or triethylamine, at room temperature or a slightly elevated temperature. Upon completion of the reaction, the reaction solution is, in general, separated from insoluble constituents and poured into a large excess of 4% strength aqueous hydrochloric acid. The product that has precipitated is then filtered off by suction and washed neutral, and the filter residue is dried under reduced pressure or in a circulating air oven at a moderately elevated temperature.

Inert solvents, such as ethers or ketones, are preferably used when reacting the monomeric naphthoquinone diazide sulfonic acid-bis-hydroxyalkyl amides with diisocyanates, in the presence of appropriate catalysts, such as dibutyl tin dilaurate or diaza bicyclooctane, at room temperature or a moderately elevated temperature. Final treatment and isolation of the polyurethanes is accomplished analogously to the polyesters mentioned above.

In the above-described reactions, the monomeric naphthoquinone diazide diol can be partially replaced by one or more other diol components, the procedure remaining otherwise the same.

The binders used in many positive materials based on naphthoquinone diazides can also be added to the compositions according to the present invention containing the novel naphthoquinone diazides. The type and quantity of the binders can vary depending on the intended use. Preference is given to binder proportions, based on total solids, between about 0% and 95%, in particular about 0 to 80%. Suitable binders include novolaks and polymeric binders with lateral phenolic hydroxyl groups, such as the polymers of vinyl phenols or of esters and amides of acrylic acid and methacrylic acid, for example, with hydroquinone, pyrocatechol, resorcinol, pyrogallol or aminophenols. In addition to the homopolymers, copolymers of the indicated monomers with each other or with other polymerizable monomers, such as styrene, methyl methacrylate, methyl acrylate, biphenylyl methacrylate or biphenylyl acrylate can also be employed as binders in the compositions according to the present invention. It is also possible to use mixtures of the polymers with novolaks.

For coating a support suitable for the preparation of the recording material according to the invention, the compositions are, in general, dissolved in a solvent. The choice of solvents should be matched to the intended coating method, the layer thickness and the drying conditions. Suitable solvents for the composition of the present invention are ketones such as butanone or N-methyl-pyrrolidone; alcohol ethers such as 2-ethoxy-ethanol or 1-ethoxy-propan-2-ol; alcohol ether acetates such as 2-ethoxy-ethylacetate or 2-ethoxy-propylacetate; and esters such as butyl acetate. It is also possible to use solvent mixtures, which may additionally contain, among others, xylene. In principle, all solvents can be used that do not irreversibly react with the layer components.

To meet special requirements, such as adhesion, smoothness of surface, specific absorption characteristics, and so on, the photosensitive composition can additionally contain small amounts (up to about 2%) of substances such as wetting agents, adhesion promoters and dyes. In addition, non-polymeric naphthoquinone diazide derivatives can be added to the photosensitive composition.

Any materials customarily employed in lithographic processes can be used as supports for the photosensitive composition. Examples that may be mentioned are metals such as aluminum supports for offset printing plates, that have been subjected to an appropriate pretreatment or copper-clad insulating boards for the fabrication of circuit boards, plastic films which may also serve as intermediary layer supports, and the supports and surfaces used in the production of microelectronic components, for example, silicon which may be oxidized on its surface or implanted with suitable dopants, silicon nitride, polysilicon, polyimides or metals, such as aluminum.

The coating of the support material is carried out in a known manner by spin-coating, spraying, roller coating, dipping, coating by means of slot dies, doctor blades or coating with the aid of a curtain coater.

For exposure, the customary light sources are employed, for example, mercury vapor lamps, which may also be doped with metal halides. Radiation sources emitting radiation of relatively high energy, for example, lasers or exposure apparatus operating with X-rays or electron beams are also suitable.

The aqueous-alkaline solutions used for development remove the areas of the photosensitive layer which have been struck by light, and thus produce a positive image of the original. Suitable developers comprise aqueous-alkaline solutions that are free from metal ions, or they may contain metal ions such as sodium and/or potassium ions. The developer solutions may be buffered, for example, with silicate, borate or phosphate solutions or with suitable mixtures of salt solutions and they may also contain small amounts of surfactants and solvents.

The radiation-sensitive compositions according to the present invention are used in lithographic processes, for example, in the fabrication of integrated circuits or of discrete electronic components. In these applications, they serve as a masking material in various process steps, for example, in the etching of the layer support, the implantation of the layer support with ions, or the deposition of materials on the layer support. The radiation-sensitive compositions of the invention are also suitable for use in the production of printing forms and can be employed in the fabrication of circuit boards.

Below, examples of 1,2-naphthoquinone-2-diazide-sulfonic acid amides according to the invention are given and photosensitive compositions according to the invention are described. First, Tables I to V specify compounds of the invention, which have been prepared in accordance with the above-indicated general instruction. In application examples 1 to 13 a number of these compounds are used as photosensitive substances in positive-working photosensitive recording materials. In the examples, quantities are, as a rule, specified as parts by weight (pbw). Quantitative proportions and percentages are to be understood as weight units, unless otherwise stated.

TABLE I

Compounds of formula I with D = 1,2-naphthoquinone-2-diazide-5-sulfonyl

| Compound No. | $R^1$ | $R^2$ | Analysis calc. | (%) found |
|---|---|---|---|---|
| 1 | $CH_2$ | $CH_2OH$ | C 49.84 | 49.6 |
| | | | H 4.48 | 4.6 |
| | | | N 12.46 | 12.3 |
| | | | S 9.50 | 9.5 |
| 2 | $CH(CH_3)$ | $CH(CH_3)OH$ | C 52.59 | 52.6 |
| | | | H 5.24 | 5.4 |
| | | | N 11.50 | 11.5 |
| | | | S 8.77 | 8.6 |

TABLE II

Compounds of formula II with D = 1,2-naphthoquinone-2-diazide-5-sulfonyl and m = 0

| Compound No. | $R^1$ | X |
|---|---|---|
| 3 | $CH_2$ | $(CH_2)_4$ |
| 4 | $CH_2$ | $(CH_2)_7$ |
| 5 | $CH_2$ | $(CH_2)_8$ |
| 6 | $CH_2$ | $(CH_2)_{10}$ |
| 7 | $CH_2$ | 1,4-phenylene |
| 8 | $CH(CH_3)$ | $(CH_2)_4$ |
| 9 | $CH(CH_3)$ | $(CH_2)_7$ |
| 10 | $CH(CH_3)$ | $(CH_2)_8$ |
| 11 | $CH(CH_3)$ | $(CH_2)_{10}$ |

TABLE III

Compounds of formula II with D = 1,2-naphthoquinone-2-diazide-5-sulfonyl, X=NH—Y—NH and m = 0

| Compound No. | $R^1$ | Y |
|---|---|---|
| 12 | $CH_2$ | $(CH_2)_6$ |
| 13 | $CH_2$ | $CH_2—C(CH_3)_2—CH_2—CH(CH_3)—(CH_2)_2$ |
| 14 | $CH(CH_3)$ | $(CH_2)_6$ |
| 15 | $CH(CH_3)$ | $CH_2—C(CH_3)_2—CH_2—CH(CH_3)—(CH_2)_2$ |

TABLE IV

Compounds of formula II with D = 1,2-naphthoquinone-2-diazide-5-sulfonyl, $R^1$ = $CH(CH_3)$ and Y = $(CH_2)_6$

| Compound No. | $R^3$ | Molar Ratio n/m |
|---|---|---|
| 16 | $(CH_2)_4$ | 3:1 |
| 17 | $(CH_2)_4$ | 1:1 |
| 18 | $(CH_2)_4$ | 1:4 |
| 19 | $(CH_2)_6$ | 1:4 |
| 20 | $CH_2C(CH_3)_2CH_2$ | 1:1 |
| 21 | $CH_2C(CH_3)_2CH_2$ | 1:1.5 |
| 22 | $CH_2C(CH_3)_2CH_2$ | 1:2 |
| 23 | $CH_2C(CH_3)_2CH_2$ | 1:3 |
| 24 | $CH_2C(CH_3)_2CH_2$ | 1:5 |

TABLE IV-continued

Compounds of formula II with D = 1,2-naphthoquinone-2-diazide-5-sulfonyl, $R^1$ = CH(CH$_3$) and Y = (CH$_2$)$_6$

| Compound No. | $R^3$ | Molar Ratio n/m |
|---|---|---|
| 25 | C(CH$_3$)$_2$CH$_2$CH(CH$_3$) | 1:1 |
| 26 | C(CH$_3$)$_2$CH$_2$CH(CH$_3$) | 1:1.5 |
| 27 | C(CH$_3$)$_2$CH$_2$CH(CH$_3$) | 1:2 |
| 28 | C(CH$_3$)$_2$CH$_2$CH(CH$_3$) | 1:5 |
| 29 | (CH$_2$)$_2$—O—(CH$_2$)$_2$—O—(CH$_2$)$_2$ | 1:1 |

TABLE V

Compounds of formula II with D = 1,2-naphthoquinone-2-diazide-5-sulfonyl, $R^1$ = CH(CH$_3$) and Y = 2,2,4-trimethyl-hexamethylene

| Compound No. | $R_3$ | Molar Ratio n/m |
|---|---|---|
| 30 | (CH$_2$)$_4$ | 3:1 |
| 31 | (CH$_2$)$_4$ | 1:1 |
| 32 | (CH$_2$)$_4$ | 1:4 |
| 33 | (CH$_2$)$_4$ | 1:9 |
| 34 | (CH$_2$)$_6$ | 1:1 |
| 35 | (CH$_2$)$_6$ | 1:4 |
| 36 | CH$_2$C(CH$_3$)$_2$CH$_2$ | 1:1 |
| 37 | CH$_2$C(CH$_3$)$_2$CH$_2$ | 1:1.5 |
| 38 | CH$_2$C(CH$_3$)$_2$CH$_2$ | 1:2 |
| 39 | CH$_2$C(CH$_3$)$_2$CH$_2$ | 1:5 |
| 40 | C(CH$_3$)$_2$CH$_2$CH(CH$_3$) | 1:1 |
| 41 | C(CH$_3$)$_2$CH$_2$CH(CH$_3$) | 1:1.5 |
| 42 | C(CH$_3$)$_2$CH$_2$CH(CH$_3$) | 1:2 |
| 43 | C(CH$_3$)$_2$CH$_2$CH(CH$_3$) | 1:5 |
| 44[x] | (CH$_2$)$_6$ | 1:1 |

[x] D = 1,2-naphthoquinone-2-diazide-4-sulfonyl

EXAMPLE 1

An electrolytically grained and anodized aluminum layer support is coated with a coating solution of
  4.8 pbw compound 2 in
  95.2 pbw of butanone
to give a layer weight of 1.20 g/m$^2$ when dried. After drying, the coated printing plate is exposed for 90 seconds, using a 5 kW metal halide lamp arranged at a distance of 120 cm, under an original which contains line and screen patterns and also a continuous-tone step wedge with 13 steps, the optical densities of which increase by 0.15 from one step to the next, and is developed for 8 seconds with a developer composed of
  3.7 pbw of sodium metasilicate×9H$_2$O and
  0.1 pbw of sodium lauryl ether polyglycol sulfate in
  96.2 pbw of water,
the exposed portions of the layer being removed in the process. A printing form is obtained which shows 4 clean wedge steps in the continuous-tone wedge.

EXAMPLE 2

An electrolytically grained and anodized aluminum layer support is coated with a coating solution of
  12.3 pbw of compound 12 and
  6.1 pbw of compound 6 in
  81.6 pbw of tetrahydrofuran
to give a layer weight of 1.28 g/m$^2$ when dried. After drying, the coated printing plate is exposed for 150 seconds under the original described in Example 1, using a 5 kW metal halide lamp arranged at a distance of 120 cm and is developed for 1 minute with a developer composed of
  5.2 pbw of sodium metasilicate×9H$_2$O and
  0.1 pbw of wetting agent as in Example 1 in
  94.7 pbw of water,
the exposed portions of the layer being removed in the process. A printing form is obtained which shows 3 clean wedge steps in the continuous-tone wedge.

EXAMPLE 3

An electrolytically grained and anodized aluminum layer support is coated with a coating solution of
  2.2 pbw of compound 3 and
  1.1 pbw of compound 12 in
  96.6 pbw of tetrahydrofuran
to give a layer weight of 0.97 g/m$^2$ after drying. The coated printing plate is exposed as in Example 2 and developed for 1 minute with a developer composed of
  2.1 pbw of sodium hydroxide and
  1.5 pbw of boric acid in
  96.4 pbw of water,
the exposed portions of the layer being removed in the process. A printing form is obtained which shows 4 clean wedge steps in the continuous-tone wedge.

EXAMPLE 4

An electrolytically grained and anodized aluminum layer support is coated with a coating solution of
  3.85 pbw of compound 13 in
  96.15 pbw of 2-methoxy-ethanol
to give a layer weight of 0.63 g/m$^2$ after drying. The coated printing plate is exposed as in Example 2 and developed for 1 minute with a developer composed of
  6.5 pbw of sodium metasilicate×9H$_2$O and
  0.1 pbw of wetting agent as in Example 1 in
  93.4 pbw of water,
the exposed portions of the layer being removed in the process. A printing form is obtained which shows 4 clean wedge steps in the continuous-tone wedge.

EXAMPLE 5

An electrolytically grained and anodized aluminum layer support is coated with a coating solution of
  5.7 pbw of compound 8 in
  96.3 pbw of butanone
to give a layer weight of 1.15 g/m$^2$ after drying. The coated printing plate is exposed as in Example 1, except that the exposure time is 75 seconds. The exposed plate is developed for 15 seconds with a developer composed of
  0.43 pbw of sodium metasilicate×9H$_2$O and
  0.1 pbw of wetting agent as in Example 1 in
  99.47 pbw of water,
the exposed portions of the layer being removed in the process. A printing form is obtained which shows 4 clean wedge steps in the continuous-tone wedge.

EXAMPLE 6

An electrolytically grained and anodized aluminum layer support is coated with a coating solution of
  3.1 pbw of compound 14 in
  96.9 pbw of butanone
to give a layer weight of 0.66 g/m$^2$ after drying. The coated printing plate is exposed as in Example 1 and developed for 5 seconds with a developer composed of
  7.2 pbw of sodium metasilicate×9H$_2$O and
  0.1 pbw of wetting agent as in Example 1 in
  92.7 pbw of water,
the exposed portions of the layer being removed in the process. A printing form is obtained which shows 4 clean wedge steps in the continuous-tone wedge.

EXAMPLE 7

An electrolytically grained and anodized aluminum layer support is coated with a coating solution of
3.85 pbw of compound 15 in
96.15 pbw of butanone
to give a layer weight of 0.91 g/m² after drying. The coated printing plate is exposed as in Example 1, except that the exposure time is 100 seconds. The exposed plate is developed for 1 minute with a developer composed of
6.5 pbw of sodium metasilicate×9H₂O and
0.1 pbw of wetting agent as in Example 1 in
93.4 pbw of water,
the exposed portions of the layer being removed in the process. A printing form is obtained which shows 2 clean wedge steps in the continuous-tone wedge.

EXAMPLE 8

An electrolytically grained and anodized aluminum layer support is coated with a coating solution of
3.85 pbw of compound 25 in
96.15 pbw of butanone
to give a layer weight of 0.92 g/m² after drying. The coated printing plate is exposed as in Example 1 but, in this case, for 85 seconds and is developed for 1 minute with a developer composed of
5.3 pbw of tetramethylammoniumhydroxide in
94.7 pbw of water,
the exposed portions of the layer being removed in the process. A printing form is obtained which shows 3 clean wedge steps in the continuous-tone wedge.

EXAMPLE 9

An electrolytically grained and anodized aluminum layer support is coated with a coating solution of
3.85 pbw of compound 36 in
96.15 pbw of butanone
to give a layer weight of 0.87 g/m² after drying. The coated printing plate is exposed as in Example 8 and developed for 1 minute with the developer indicated in Example 8, the exposed portions of the layer being removed in the process. A printing form is obtained which shows 3 clean wedge steps in the continuous-tone wedge.

EXAMPLE 10

An electrolytically grained and anodized aluminum layer support is coated with a coating solution of
3.85 pbw of compound 23 in
96.15 pbw of butanone
to give a layer weight of 0.90 g/m² after drying. The coated printing plate is exposed as in Example 1, except that the exposure time is 70 seconds. The exposed plate is developed for 1 minute with the developer indicated in Example 4, the exposed portions of the layer being removed in the process. A printing form is obtained which shows 4 clean wedge steps in the continuous-tone wedge. A similar result is obtained when the same quantity of compound 28 or of compound 29 is, in each case, substituted for compound 23 in the specified formulation.

EXAMPLE 11

An electrolytically grained and anodized aluminum layer support is coated with a coating solution of
1.9 pbw of compound 15 and
1.9 pbw of polyvinylphenol (Maruzen Oil) in
38.5 pbw of butanone and
57.7 pbw of 2-methoxy-ethanol
to give a layer weight of 1.00 g/m² after drying. The coated printing plate is exposed as in Example 8 and developed for 1 minute with the developer indicated in Example 4, the exposed portions of the layer being removed in the process. A printing form is obtained which shows 4 clean wedge steps in the continuous-tone wedge.

EXAMPLE 12

A silicon disk is spin-coated with a coating solution comprising
4.6 pbw of compound 1 and
15.7 pbw of a cresol-formaldehyde novolak (melting range 122° to 132° C., according to DIN 53 181) in
30.9 pbw of tetrahydrofuran and
48.8 pbw of N-methylpyrrolidone
to give a layer thickness of 1.8 μm after drying. The layer thus obtained has a good photosensitivity. The suitable developer (an 0.14 normal, buffered NaOH solution) is strongly diluted as compared with conventional developers and produces a lower pollution of waste water.

A similar result is obtained when compound 2 is substituted for compound 1 in the specified formulation.

EXAMPLE 13

An electrolytically grained and anodized aluminum layer support is coated with a coating solution of
3.9 pbw of compound 44 in
96.1 pbw of 2-methoxy-ethanol
to give a layer weight of 0.72 g/m² after drying. The coated printing plate is exposed as in Example 2 and developed for 1 minute with the developer indicated in Example 4, the exposed portions of the layer being removed in the process. A printing form is obtained which shows 4 clean wedge steps in the continuous-tone wedge.

What is claimed is:

1. A compound of the general formula II

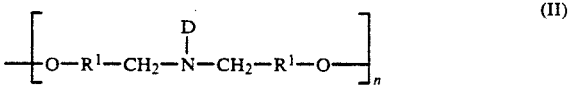

in which
D denotes a 1,2-naphthoquinone-2-diazide-4-sulfonyl or -5-sulfonyl radical,
R₁ denotes an alkylene group with 1 to 3 carbon atoms,
X denotes an alkylene group with 2 to 12 carbon atoms, an arylene group with 6 to 10 carbon atoms or a group of the formula

wherein
Y is an alkylene group with 2 to 12 carbon atoms or an arylene group with 6 to 14 carbon atoms,
R³ denotes an alkylene group with 2 to 12 carbon atoms, which may be interrupted by ether oxygen atoms,
n is a number form 1 to 40 and
m is a number from 0 to 50, the ratio m:(m+n) being from 0:100 to 95:100.

2. A compound as claimed in claim 1, wherein Y is an alkylene group having 6 to 10 carbon atoms.

3. A compound as claimed in claim 1, wherein $R^3$ is an alkylene group having 4 to 8 carbon atoms, which may be interrupted by either oxygen atoms.

4. A compound as claimed in claim 1, wherein the ratio m:(m+n) is from 10:100 to 95:100.

5. A photosensitive composition, comprising, in admixture:
a polymeric binder insoluble in water and soluble in organic solvents and in aqueous-alkaline solutions, in an amount sufficient to form a uniform film when the photosensitive composition is coated on a support; and
a photosensitive 1,2-naphthoquinone-2-diazide sulfonic acid amide in an amount sufficient to increase the solubility of those portions of the composition that are exposed to actinic radiation, said 1,2-naphthoquinone-2-diazide sulfonic acid amide being selected from the group consisting of a compound of the general formula I

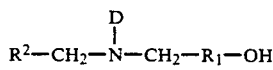
(I)

in which
D denotes a 1,2-naphthoquinone-2-diazide -4-sulfonyl or -5-sulfonyl radical,
$R_1$ denotes an alkylene group with 1 to 3 carbon atoms and
$R^2$ denotes a hydrogen atom, an alkyl group with 1 to 3 carbon atoms or a group $R^1$—OH,
and a compound of the general formula II

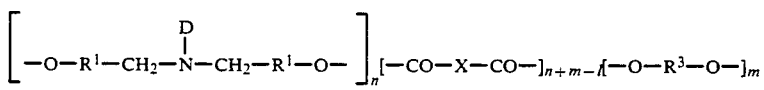
(II)

in which
X denotes an alkylene group with 2 to 12 carbon atoms, an arylene group with 6 to 10 carbon atoms or a group of the formula

NH-Y-NH, wherein
Y is an alkylene group with 2 to 12 carbon atoms or an arylene group with 6 to 14 carbon atoms,
$R^3$ denotes an alkylene group with 2 to 12 carbon atoms, which may be interrupted by either oxygen atoms,
n is a number from 1 to 40 and
m is a number from 0 to 50, the ratio m:(m+n) being from 0:100 to 95:100 and
$R^1$ and D is defined above.

6. A photosensitive recording material, comprising:
a support; and
a photosensitive layer comprising a composition as claimed in claim 5.

7. A compound according to general formula II of claim 1, wherein Y is a mononuclear arylene group.

8. A compound according to general formula II of claim 1, wherein Y is an alkylene group having from 4 to 10 carbon atoms.

9. A compound according to general formula II of claim 1, wherein X is a phenyl group.

10. A compound according to general formula II of claim 1, wherein X is an alkylene group having from 4 to 10 carbon atoms.

11. A compound according to general formula II of claim 1, wherein Y is a mononuclear arylene group or an alkylene group having from 4 to 10 carbon atoms.

12. A compound according to claim 11, wherein X is a phenyl group or an alkylene group having from 4 to 10 carbon atoms.

13. A compound according to general formula II of claim 1, wherein $R^3$ is an alkylene group having from 4 to 10 carbon atoms.

14. A compound according to general formula II of claim 1, wherein $R^3$ is an alkylene group having from 4 to 8 carbon atoms.

15. A compound according to claim 1, wherein the ratio m:(m+n) is from 25:100 to 99:100.

16. A compound of the general formula II

(II)

in which
D denotes a 1,2-naphthoquinone-2-diazide-4-sulfonyl or -5-sulfonyl radical,
$R_1$ denotes an alkylene group with 1 to 3 carbon atoms,
X denotes an alkylene group with 2 to 12 carbon atoms, an arylene group with 6 to 10 carbon atoms or a group of the formula

NH-Y-NH, wherein
Y is an alkylene group with 2 to 12 carbon atoms or an arylene group with 6 to 14 carbon atoms,
$R^3$ denotes an alkylene group with 2 to 12 carbon atoms, which may be interrupted by either oxygen atoms,
n is a number form 1 to 40 and
m is a number from 0 to 50, the ratio m:(m+n) being from 0:100 to 95:100.

17. A photosensitive composition as claimed in claim 5, wherein the 1,2-naphthoquinone-2-diazide sulfonic acid amide is a compound according to Formula I.

18. A photosensitive composition as claimed in claim 5, wherein the 1,2-naphthoquinone-2-diazide sulfonic acid amide is a compound according to Formula II.

19. A photosensitive composition as claimed in claim 5, comprising from about 5 to 100% by weight, based on its non-volatile components, of the 1,2-naphthoquinone-2-diazide sulfonic acid amide.

20. A photosensitive composition as claimed in claim 5, wherein the 1,2-naphthoquinone-2-diazide sulfonic acid amide is derived from a secondary amine.

21. A compound as claimed in claim 1, wherein he 1,2-naphthoquinone-2-diazide sulfonic acid amide is derived from a secondary amine.

* * * * *